United States Patent
Pile-Spellman et al.

(10) Patent No.: US 10,773,009 B2
(45) Date of Patent: Sep. 15, 2020

(54) METHODS AND SYSTEMS FOR THE DELIVERY OF DISSOLVED GASES AND DE-GASSING MEDICAL FLUID LINES

(71) Applicant: Hybernia Medical LLC, Pelham, NY (US)

(72) Inventors: John Pile-Spellman, Pelham, NY (US); Jae H. Choi, Mineola, NY (US)

(73) Assignee: TRANSLUMINAL SYSTEMS, LLC, New Rochelle, NY (US)

( * ) Notice: Subject to any disclaimer, the term of this patent is extended or adjusted under 35 U.S.C. 154(b) by 636 days.

(21) Appl. No.: 15/386,219

(22) Filed: Dec. 21, 2016

(65) Prior Publication Data
US 2017/0173247 A1    Jun. 22, 2017

Related U.S. Application Data (60) Provisional application No. 62/270,216, filed on Dec. 21, 2015.

(51) Int. Cl.
*A61M 1/36*    (2006.01)
*A61M 5/14*    (2006.01)
(Continued)

(52) U.S. Cl.
CPC .......... *A61M 1/363* (2014.02); *A61M 1/1603* (2014.02); *A61M 1/1629* (2014.02);
(Continued)

(58) Field of Classification Search
CPC .............. A61M 1/1603; A61M 1/1629; A61M 1/1698; A61M 1/32; A61M 1/3626; A61M 1/363; A61M 1/3638; A61M 1/3652; A61M 2202/0225; A61M 2202/0275; A61M 2205/3368; A61M 2205/3379; A61M 2205/36; A61M 2205/52; A61M 39/223
See application file for complete search history.

(56) References Cited

U.S. PATENT DOCUMENTS 5,149,321 A * 9/1992 Klatz ................. A01N 1/02
604/500
5,896,854 A * 4/1999 Bliss ................. A61M 16/024
128/200.24
(Continued)

FOREIGN PATENT DOCUMENTS

CN        102500006 A  *  6/2012

OTHER PUBLICATIONS

CN-102500006-B—Machine Translation; accessed on May 9, 2019 by USPTO on Google Patents (Year: 2012).*

*Primary Examiner* — Benjamin J Klein
(74) *Attorney, Agent, or Firm* — Antonio Papageorgiou; Meister Seelig & Fein LLP (57) ABSTRACT

A method and system for infusing medical liquid with gasses, the system comprising a gas source, a vacuum pump, a temperature-controlled container including a fluid reservoir coupled to the gas source and the vacuum pump, a heating and cooling system, and a sonicator, and a controller configured to de-gas a liquid in the fluid reservoir by activating the vacuum pump, re-gas the liquid in the fluid reservoir by releasing gas from the gas source to the fluid reservoir via a first fluid line, and deliver the re-gassed liquid from the fluid reservoir to a catheter via a second fluid line.

19 Claims, 5 Drawing Sheets

(51) Int. Cl.
*A61M 1/16* (2006.01)
*A61M 1/32* (2006.01)
*A61M 39/22* (2006.01)

(52) U.S. Cl.
CPC ............ *A61M 1/1698* (2013.01); *A61M 1/32* (2013.01); *A61M 1/3626* (2013.01); *A61M 1/3638* (2014.02); *A61M 1/3652* (2014.02); *A61M 5/14* (2013.01); *A61M 39/223* (2013.01); *A61M 2202/0225* (2013.01); *A61M 2202/0275* (2013.01); *A61M 2205/3368* (2013.01); *A61M 2205/3379* (2013.01); *A61M 2205/36* (2013.01); *A61M 2205/52* (2013.01); *A61M 2205/702* (2013.01)

(56) References Cited

U.S. PATENT DOCUMENTS

2003/0080002 A1* 5/2003 Taagaard ................. G01N 7/00
   205/782
2005/0147958 A1* 7/2005 Hassanein ................. A01N 1/02
   435/1.1

* cited by examiner

METHODS AND SYSTEMS FOR THE DELIVERY OF DISSOLVED GASES AND DE-GASSING MEDICAL FLUID LINES

CROSS REFERENCE TO RELATED APPLICATION

This application claims the priority of U.S. Provisional Application No. 62/270,216, entitled "METHOD AND SYSTEMS FOR THE DELIVERY OF DISSOLVED GASES," filed on Dec. 21, 2015, the disclosure of which is hereby incorporated by reference in its entirety.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

Field of the Invention

The present application relates to systems and methods for the delivery of a prescribed amount of liquids containing dissolved medical gases directly via the arterial system, and mitigating the harm of inadvertent injection of air during medical procedures, particularly when flushing the lines with fluids, prior to insertion into the body.

Description of the Related Art

In many clinical conditions it is desirable to administer gasses to a patient for therapeutic purposes. For example, oxygen may be delivered to a patient for the by purpose of increasing the partial pressure of oxygen within the patient's blood. In certain conditions, oxygenators may be employed to administer oxygen directly to a patient's bloodstream. Examples of oxygenators include those disclosed in U.S. Pat. Nos. 3,934,982, and 4,440,723 The oxygenators combine oxygen-containing gas with blood and return the oxygenated blood to a blood vessel or blood source. The administration of oxygen may provide benefit in terms of alleviating a patient's symptoms, and helping preserve organ function, however, the metabolic state of the cells of the patient's organ or organs may remain normal or above normal.

Inadvertent injection of air into a body, particularly into the arterial circulation—even in very small amounts can lead to devastating complications. Clearing air from medical devices about to be inserted (e.g., stents, coil) and the routine preparation of tubing used for subsequent fluid injection into arteries is particularly problematic as small bubbles adhere to the wall of the tubing, and must be dislodged by shacking the tube while flushing it and holding the distal end up while confirming the bubbles have been flushed form the tube. For complex, non-visualizable devices and tubing, this is even more problematic.

Hypothermia has been shown to reduce metabolic demands on organs, such as the heart and/or the brain. Hypothermia may also provide protective effects on a patient's organs by preventing undesirable spread of cellular death or injury. One method for inducing hypothermia of the heart or entire body is through the use of a heat exchange catheter that is inserted into a blood vessel and used to cool blood flowing through that blood vessel.

Existing devices do not combine the benefits of providing gasses and inducing hypothermia via the bloodstream. Thus, there remains a need in the art for improving organ preservation in patients that suffer from compromised organ functions.

SUMMARY OF THE INVENTION

The present application provides systems and non-transitory computer readable media comprising computer program code for the delivery of liquids containing dissolved, clinically useful medical gases in a prescribed fashion.

One embodiment includes a system for infusing medical liquid with gasses. The system comprises a gas source, a vacuum pump, a temperature-controlled container including a fluid reservoir coupled to the gas source and the vacuum pump, a heating and cooling system, and a sonicator, and a controller configured to de-gas a liquid in the fluid reservoir by activating the vacuum pump, re-gas the liquid in the fluid reservoir by releasing gas from the gas source to the fluid reservoir via a first fluid line, and deliver the re-gassed liquid from the fluid reservoir to a catheter via a second fluid line.

The controller may be further configured to de-gas the liquid in the fluid reservoir by enabling the heating and cooling system to heat the fluid reservoir, and activating the sonicator to sonificate the fluid reservoir. The controller may also be further configured to re-gas the liquid in the fluid reservoir by enabling the heating and cooling system to cool the fluid reservoir, and activating the sonicator to sonificate the fluid reservoir. The gas may comprise a gas selected from the group consisting of oxygen, carbon dioxide, and nitric oxide. The system may further include sensors to detect bubbles, gas concentration, and temperature of the liquid.

In one embodiment, the system further comprises a device that flushes the first fluid line and the second fluid line with safe gases. The safe gases may be a gas that is quickly metabolized, highly soluble, and non-toxic. The safe gases may comprise a gas selected from the group consisting of carbon dioxide and oxygen. A further embodiment of the system may include the controller further configured to flush the first fluid line and the second fluid line with the liquid subsequent to de-gassing the liquid.

The non-transitory computer readable media comprises computer program code for de-gassing a liquid in a fluid reservoir by activating a vacuum pump, the fluid reservoir coupled to a gas source and the vacuum pump, and is comprised in a temperature-controlled container that includes a heating and cooling system and a sonicator. The non-transitory computer readable media further comprises computer program code for re-gassing the liquid in the fluid reservoir by releasing gas from the gas source to the fluid reservoir via a first fluid line, and computer program code for delivering the re-gassed liquid from the fluid reservoir to a catheter via a second fluid line.

The non-transitory computer readable media may further comprise computer program code for de-gassing the liquid in the fluid reservoir by enabling the heating and cooling system to heat the fluid reservoir and activating the sonicator to sonificate the fluid reservoir. In another embodiment, the non-transitory computer readable media may further comprise computer program code for re-gassing the liquid in the fluid reservoir by enabling the heating and cooling system to cool the fluid reservoir, and activating the sonicator to sonificate the fluid reservoir. The gas may comprise a gas selected from the group consisting of oxygen, carbon dioxide, and nitric oxide. According to yet another embodiment, the non-transitory computer readable media may further comprise computer program code for detecting bubbles, gas concentration, and temperature of the liquid. The non-transitory computer readable media may also include computer program code for flushing the first fluid line and the second fluid line with the liquid subsequent to de-gassing the liquid.

BRIEF DESCRIPTION OF THE DRAWINGS

The invention is illustrated in the figures of the accompanying drawings which are meant to be exemplary and not limiting, in which like references are intended to refer to like or corresponding parts.

DETAILED DESCRIPTION OF THE INVENTION

Subject matter will now be described more fully hereinafter with reference to the accompanying drawings, which form a part hereof, and which show, by way of illustration, exemplary embodiments in which the invention may be practiced. Subject matter may, however, be embodied in a variety of different forms and, therefore, covered or claimed subject matter is intended to be construed as not being limited to any example embodiments set forth herein; example embodiments are provided merely to be illustrative. It is to be understood that other embodiments may be utilized and structural changes may be made without departing from the scope of the present invention. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of exemplary embodiments in whole or in part.

The present application addresses a medical need of being able to deliver critical gases in a dissolved state, and in known concentrations, to human tissues via a catheter in an artery perfusing the area of the tissues. Key metabolically active gases such as oxygen ($O_2$), carbon dioxide ($CO_2$) and ultra-short half-life bio-messenger molecule gases such as nitric oxide (NO), etc., can be delivered by such means. One embodiment includes markedly increasing $O_2$ delivery into ischemic tissues during intra-arterial (IA) therapy by delivering a concentrated amount of $O_2$, in a low viscosity fluid, at a high partial pressure in ischemic tissues with low blood flow states, (myocardial infarctions, cerebral ischemia, etc.).

Accordingly, a fluid delivery device may be provided to markedly increase the amount of $O_2$ dissolved in a fluid that may be delivered into an artery of a patient. The device may first de-gases the injection fluid/liquid reserve, stripping it of its, e.g., nitrogen ($N_2$) and $O_2$ gases. This is preferably done with heat, vacuum (e.g., Henry's Law), or a combination of the two with or without agitation, (e.g., sonification, etc.). The fluid/liquid may then be re-gassed with, e.g. 100% oxygen. This fluid-gas mixture can be considered mono-saturated fluid, since all of potential gas solubility of the fluid at that temperature and pressure is taken up by the single gas. Additional $O_2$ can be dissolved with increased pressure and cooling. It is possible to repeat the process to enhance the total amount of $O_2$ contained in the liquid. In blood normally, the non-heme containing fluid carries only 3% of the oxygen which is not enough to support life. However, using the method described in this application, the amount of $O_2$ carried by non-heme fluid/liquids can be markedly increased to meaningfully contribute to support tissue viability. Additionally, these methods being used in conjunction with hypothermic treatment that decreases $O_2$ demand, and the effect of the additional fluid decreasing blood viscosity also increases the $O_2$ delivered. These factors work in concert to increase the $O_2$ content of water ($H_2O$) or other fluid/liquid that may be injected from a baseline of 3% in a clinically useful amount to 50%—exceeding 100% of the needed $O_2$ for the tissue.

In an alternative embodiment, the fluid delivery device may be provided to markedly increase the amount of NO dissolved in a fluid that may be delivered into an artery of a patient.

In another embodiment of the present invention, is a flushing device for effective flushing of the fluid delivery device with oxygen ($O_2$), that is safe to inject, and quickly metabolized $O_2$, that replaces atmospheric air that is, e.g., 80% nitrogen. The flushing device can flush the distal line about to be connected to a patient with $O_2$ or $CO_2$ prior to infusion of fluid. The flushing device can also be used separate from the fluid delivery device. In such a configuration, the flushing device may include: connectors, gas micro-pore filters, and valves that assures the safe, complete and effective replacement of all prior room-air-associated-$N_2$ with $O_2$ in a line. The line may then be connected to fluid lines before inserting into the patient.

In still another embodiment of the present invention, is a flushing device for effective flushing of a fluid delivery device with $CO_2$, that is safe to inject, and highly soluble $CO_2$, that replaces atmospheric air that is, e.g., 80% nitrogen. The flushing device includes connectors, gas micro-pore filters, and valves that assure the safe, complete and effective replacement of all $N_2$ gas with $O_2$ or $CO_2$ gases. One or more of the disclosed embodiments are also applicable to non-medical uses such as clearing air from water lines.

Figure 1:
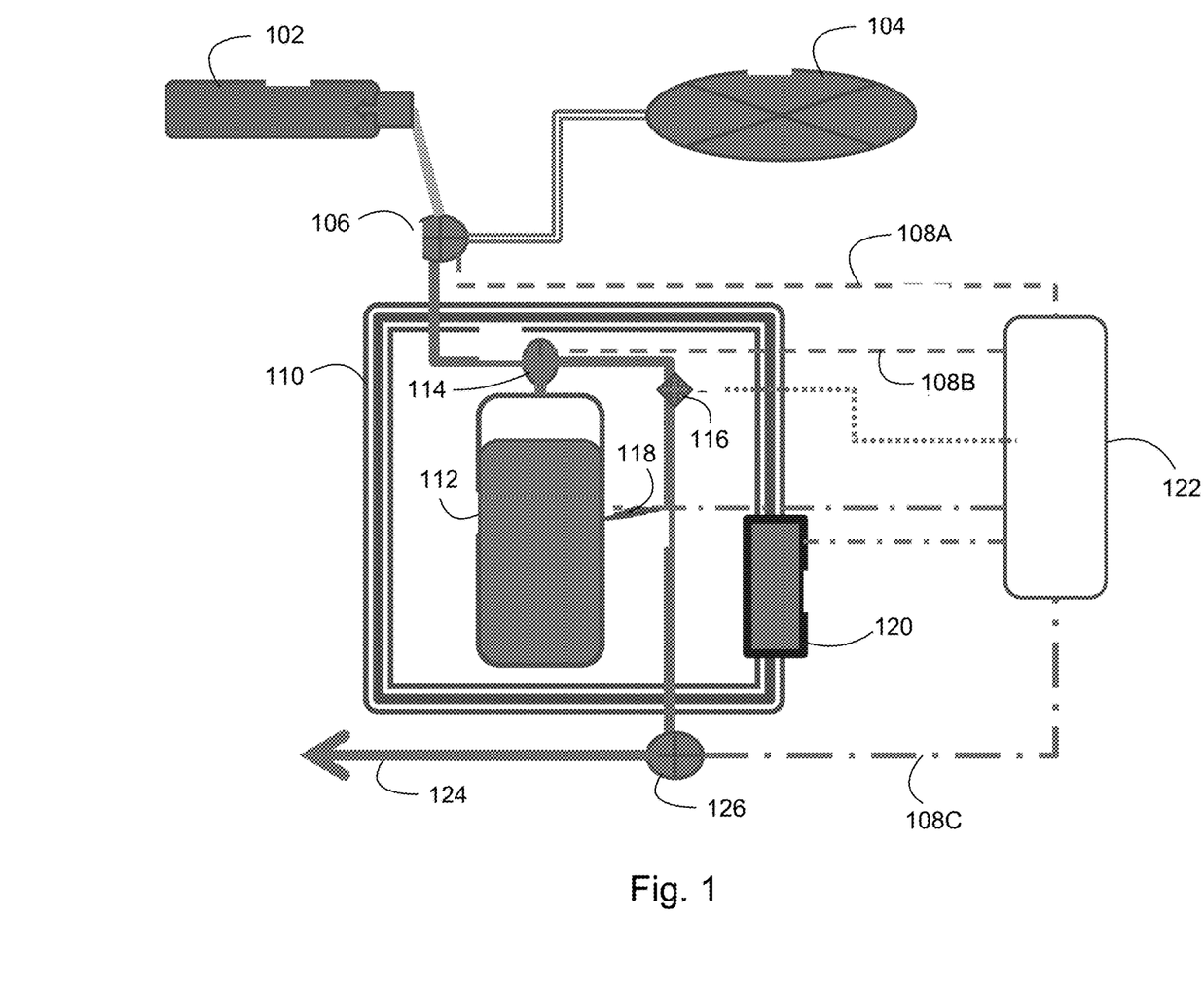
FIG. 1 depicts a system diagram according to at least one embodiment of the systems disclosed herein.
Figure 2:
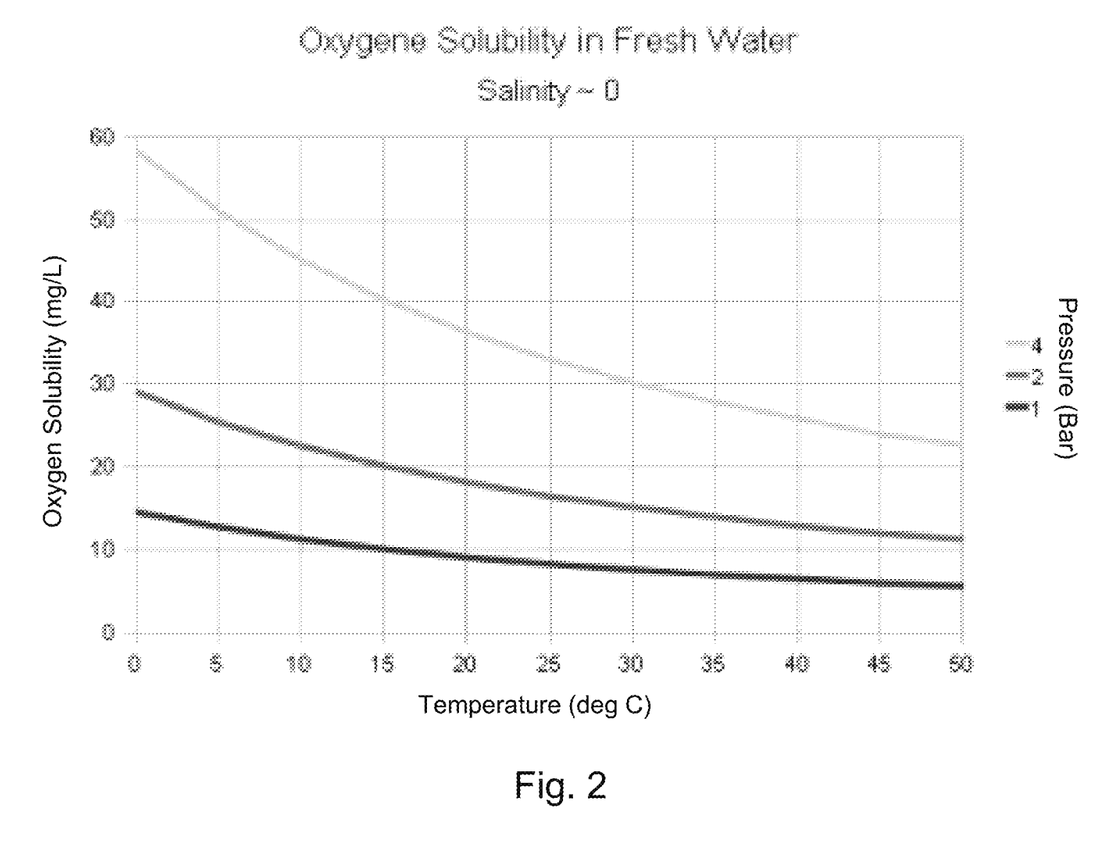
FIG. 2 depicts a chart of oxygen solubility in fresh water.

Referring to FIG. 1, in one embodiment, the system comprises a device that is able to de-gas a medical solution (fluid/liquid), and re-gas the solution with a target gas, while considering the type of solution, type of gas, temperature, and pressure, and wherever possible tissue blood flow characteristics and needs. This gas saturated solution may then be instilled into an artery for medical treatment. De-gassing of fluids can be done in a variety of ways including: A) heat stirring, B) vacuum de-gassing using an aspirator, C) vacuum de-gassing using a gas-liquid separation membrane, D) de-gassing by helium purging and E) freeze-pump-thawing cycling. All of these methods could be used, and might be used in specific clinical indications depending on the gas and the solution being used. The use of de-gassing and re-gassing with or without cooling and pressure may be used to increase the amount of gas dissolved, as shown in FIG. 2.

In the embodiment illustrated in FIG. 1, an automated (programmed controller or computer) de-gasser, and medical gas re-gasser is provided comprising a combination of a medical gas cylinder with regulator 102, vacuum pump 104, three-way valve with solenoid 106, controller connections to solenoids 108A, 108B, 108C, thermo-insulated container 110, collapsible fluid reservoir with gas/physiological layer 112, three-way valve 114 (comprising a connection from fluid reservoir 112 and a gas/vacuum and fluid pathway, with solenoid), fluid inline sensors 116 (bubble detectors, gas measure, and temperature), e.g., one coupled to a line adjacent to 114 (proximal to fluid reservoir 112) and a second coupled to a line adjacent to 124 (fluid pathway to catheter) that is distal to fluid reservoir 112, controller 122 (including a power supply), sonicator 118 with connection to controller 122, heater/chiller 120 including a temperature sensor and connection to a computer via a connection from solenoid to controller 122, three-way valve with solenoid 126, and fluid pathway to catheter 124 which may include a connector to a catheter system.

The controller 122 may be a microcontroller or processor that can be programmed to control de-gassing, re-gassing, heating/chilling, and sonication of the medical solution in the fluid reservoir 112. Controller 122 is configurable to control the solenoids associated with valves 106 and 114 via the controller connections to the solenoids 108A and 108B to establish pathways from vacuum pump 104 (to de-gas) and medical gas cylinder with regulator 102 (to re-gas) to fluid reservoir 112. The regulator of medical gas cylinder 102 may limit an amount of gas pressure allowed in fluid reservoir 112. Fluid reservoir 112 is contained within thermos-insulated container 110 comprising a heating/cooling chamber and connected to a fluid pathway (from the medical gas cylinder with regulator 102 to a catheter) and the sonicator 118. Based on readings from fluid inline sensors 116, sonicator 118 and heater/chiller 120 may be activated in conjunction with medical gas cylinder with regulator 102 to gas the medical solution in fluid reservoir 112 to a desired gas concentration. Once the medical solution reaches the desired gas concentration, the controller 122 may control valve 126 with connection 108C to deliver the gas-saturated solution to fluid pathway to catheter 124.

Figure 3:
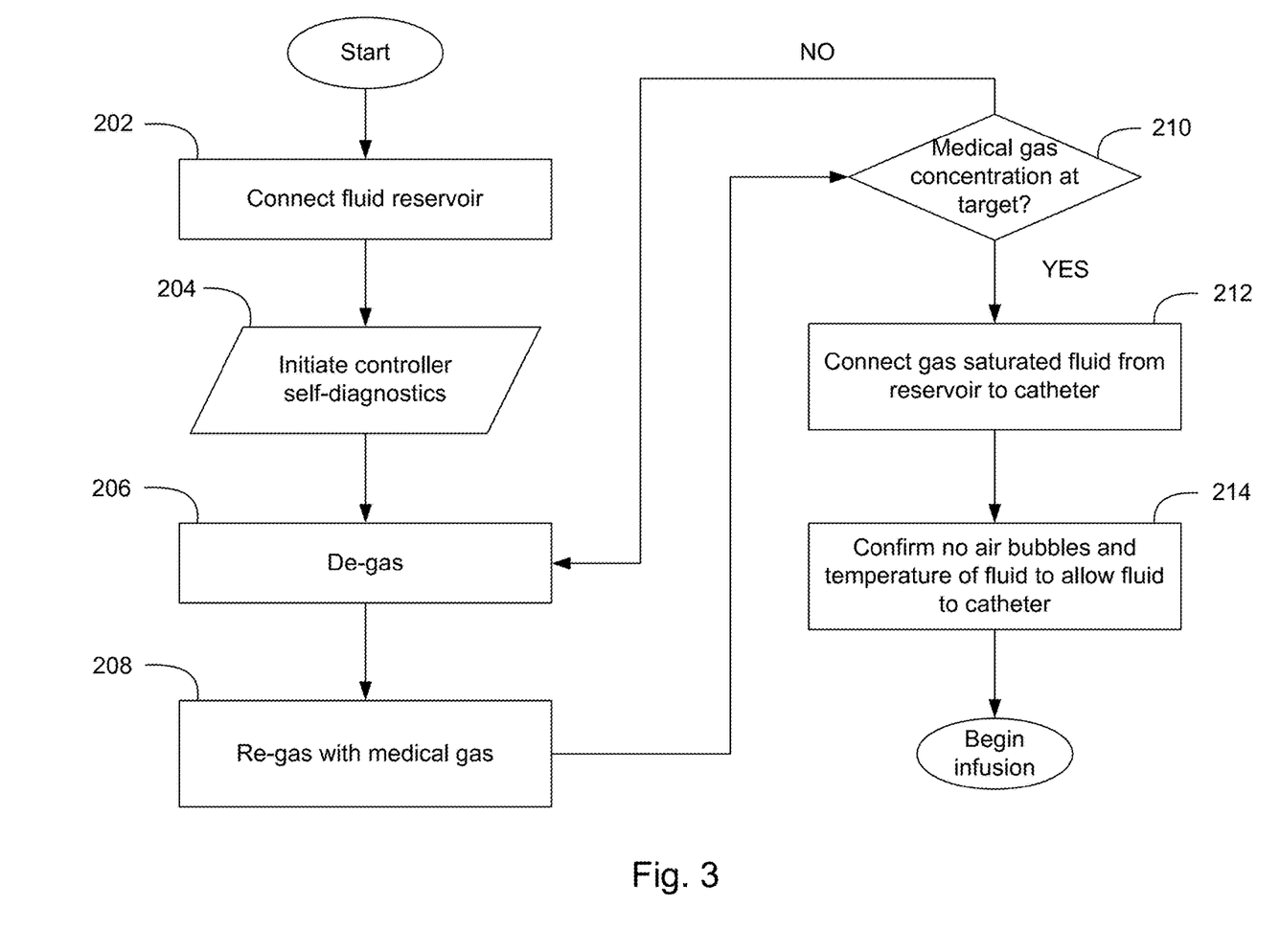
FIG. 3 depicts a flow diagram for a method according to at least one embodiment of the methods disclosed herein.

FIG. 3 presents a flowchart of a method performed by a microcontroller for controlling the enrichment of medical liquids with medical gas for delivery to a catheter line. The microcontroller may receive a signal representative of a connection with a fluid reservoir, step 202. The fluid reservoir may contain a sterile medical solution or liquid, such as, saline.

The microcontroller may then initiate self-diagnostics, step 204. Self-diagnostics may include establishing communication or electronic signaling with solenoids of fluid pathway valves to and from the fluid reservoir, and with sensors coupled to the fluid pathway of the fluid reservoir. A de-gas procedure is started, step 206. The de-gas procedure may comprise removing gas, warming, and sonicating the medical liquid. The microcontroller can open a pathway between the fluid reservoir and a vacuum pump. The microcontroller may then enable the vacuum pump to remove air from the fluid reservoir. The controller may stop the vacuum when it detects continuous fluid or the medical liquid is void of bubbles via a bubble sensor. A heater and a sonification device may be turned on by the controller until the medical liquid reaches a given temperature, such as, 50° C. for a predetermined period of time (e.g., 90 minutes or more). The controller may again open a pathway between the fluid reservoir and the vacuum pump to remove additional air from the fluid reservoir until the bubble sensor identifies continuous fluid.

The medical liquid is re-gassed with medical gas, step 208. The microcontroller may open a pathway between the fluid reservoir and a medical gas source to inflate, pump, or release medical gas to the fluid reservoir up to a regulator determined pressure (e.g., 1.25 atm). A chiller and the sonification device may be turned on by the microcontroller until temperature of the medical liquid is a given temperature, such as, −2° C. for a predetermined period of time (e.g., three hours or more). The microcontroller may again open the pathway between the fluid reservoir and the vacuum pump to remove any undissolved additional gas from the fluid reservoir until the bubble detector identifies continuous fluid.

Inline sensors may be coupled to the fluid reservoir to measure medical gas concentration in the medical liquid. The microcontroller determines whether a target concentration of the medical gas in the medical liquid has been achieved, step 210. If the target concentration has not been achieved, steps 206 and 208 may be repeated until the inline sensors indicate gas concentration at the target concentration.

When the microcontroller determines that the target concentration has been achieved, the microcontroller connects a pathway to allow the gas-saturated medical liquid to flow from the fluid reservoir to a catheter, step 212. The microcontroller may continue to cool or maintain the medical liquid at a predetermined cooling temperature. Prior to allowing the liquid to go to the catheter, the microcontroller may retrieve data readings from sensors coupled to the fluid pathway connected to the fluid reservoir to ensure that there are no air bubbles in the medical liquid and the temperature of the liquid is at the predetermined cooling temperature, step 214. Once the fluid is ready, infusion using the prepared medical liquid may begin.

The systems disclosed herein may be used in combination or combined with the Hybernia cooling catheter system, disclosed in U.S. Pat. No. 8,343,097, which is incorporated herein by reference. It can also be used with a routine catheter, or with a catheter that measures the blood flow in some different way. Additionally, although it is initially envisioned to be used in the arterial circulation, it is understood that it could be used on the venous circulation (e.g. O2 or drug delivery to the lungs, right heart, or during retro-venous perfusions (coronary sinus retro-perfusion)).

A preferred method for oxygen being dissolved in saline for IA injection is disclosed herewith. The contribution of O2 carried by injected physiological solutions has been considered clinically inconsequential because of the extremely low O2 content of most fluids, and if anything, detrimental since it dilutes the very effective O2 carrying capacity of hemoglobin (volume-to-volume, hemoglobin carries 33 times more O2 than the rest of the blood contents). The initial 21% of the O2 in air is equal to 159 mmHg of O2 at sea level. However, by the time it reaches the lungs and is in equilibrium with the blood, the partial pressures of H2O vapor and CO2 displace some of the O2 content, so that the blood partial pressure of oxygen (PaO2) is only 95-100 mmHg. Of this, the vast majority, e.g., 97%, of O2 is carried by the hemoglobin in the blood, with the "water" in the blood carrying only 3% (this 3% may be referred to in the following discussion for ease of discussion and represents 0.6 cc O2/100 cc blood). For the sake of the disclosed discussion—all material not hemoglobin may be referred to as "water" 70% even of the red blood cells' is water. For the purposes of the disclosed calculations, the O2 solubility of the other non-hem blood components may be considered equal to that of H2O. The low solubility of O2 in H2O, coupled with the low partial pressure of O2 makes normal saline a poor carrier of oxygen except under high partial pressure such as during hyperbaric treatment. Additionally, any dilution of the highly effective hemoglobin O2 carrier would have to be offset by something equally effective- and under normal conditions this is not the situation. Therefore, the contribution of O2 carried in the H2O, or other physiological solutions is clinically considered inconsequential except in uncommon condition. Although patients with tissue ischemia are often treated with 100% O2 via intubation, the beneficial effects of delivering it to the lung are profoundly blunted by a number of practical factors, including high partial pressures of H2O, and CO2, poor transfer at the alveoli, poor delivery by the circulation system, local toxicity of the alveoli to the high O2 concentrations. However, these issues are mitigated by the systems disclosed herein.

Figure 4:
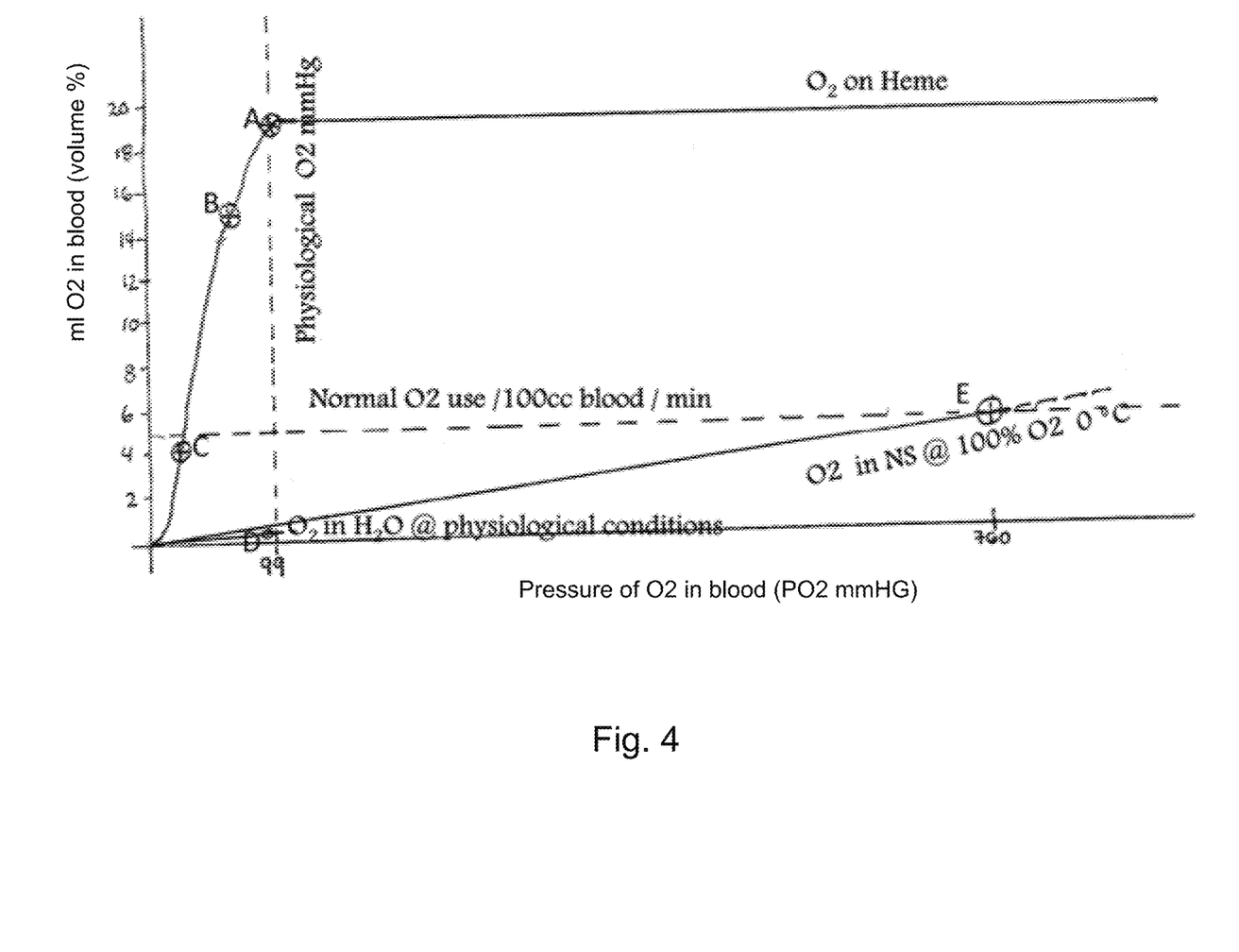
FIG. 4 depicts a chart of oxygen partial pressure vs. oxygen content.

FIG. 4 illustrates O2 partial pressure (mmHG) VS O2 content (ml/100 cc), where:
  A—20 ml of O2/100 cc of blood=normal arterial O2 content at 100 mmHg O2 tension
  B—15 ml of O2/100 cc of blood=normal venous O2 content at 60 mmHg O2 tension
  C—5 ml of O2/100 cc of blood=nadir of venous O2 content at 30 mmHG O2 tension
  D—0.33 ml of O2/100 cc of plasma (blood)=O2 content at 100 mmHG O2
  E—5 ml of O2/100 cc of normal saline=O2 content at 750 mmHG O2 tension and 0° C.

Dissolved O2 Gas at a Useful Amount:

A) De-gassing and re-gassing normal saline (NS), under about 100% O2 will bring the O2 tension up to approximately 750 mmHg, or the effective O2 up about 7.5× from about 3% to about 22.5% B) During re-gassing, lowering the temperature from about 38 C.° to about 0° C.° increases the solubility of O2 in H2O by a factor of approximately two, thus increasing the dissolved O2 from about 22.5% to about 45% of O2 content that is normally carried by blood, C) The amount of dissolved gas is directly proportional to the pressure under which it is placed (ideal gas laws). The high pressure fluid circuit used in the above-referenced Hybernia catheter system runs at about 3-15 times the atmospheric pressure.

Table A presents the effect on a liquid when replacing all other dissolved gases with O2 and cooling, thus increasing the O2 carrying from 0.34 cc O2/100 cc to 5.1 cc O2/100 cc fluid. Gas dissolved by either decreased temperature or increasing pressure may immediately come out of the solution (bubble) when the pressure is reduced.

TABLE A

| ° C. | ° F. | ml of O2/dl on room air@ 21% O2, or 158 mmHg | ml of O2/dl in arterial blood with 100 mmHg | ml of O2/dl O2 at 750 mmHg (e.g. all other gases removed) |
|---|---|---|---|---|
| 0 | 32 | 1.02 | .63 | 5.10 |
| 5 | 41 | .91 | .56 | 4.55 |
| 10 | 50 | .82 | .51 | 4.10 |
| 15 | 59 | .75 | .47 | 3.75 |
| 20 | 68 | .68 | .42 | 3.40 |
| 25 | 77 | .63 | .39 | 3.15 |
| 30 | 86 | .59 | .37 | 2.95 |
| 35 | 95 | .55 | .34 | 2.75 |
| 40 | 104 | .52 | .32 | 2.60 |

Delivering Enough O2:

It should be noted that under normal resting states, human tissue uses less than about ⅓ of the O2 delivered by the blood in the range of about 21-32% of the O2 delivered. This translates to about 4-6 cc O2/100 cc blood/min used by the tissue out of the about 19-20 cc O2/100 cc of blood/min in arterial blood available. Short term tissue viability requires significantly less—approximately ½ of this, about 10-15% of the usually delivered O2, or about 2-3 ml O2/100 cc of tissue/min. Blood normally carries 19 to 20 cc O2/100 cc of blood in the artery. The tissue extracts 4-6 cc of O2 leaving 16-13 cc of O2 in the venous blood. O2 delivery is based on the amount of blood carried times the blood flow rate times the oxygen extracted by the tissue.

As can be seen from the above calculations and graph in FIG. 4, this amount is well within the range of the device and method disclosed. And more importantly in marginal situations—even tiny augmentation of the O2 delivery can be tissue sparing. Although hemoglobin has a high carrying capacity for O2, it does this at a cost. O2 is held tightly to the hemoglobin, and much is not available even at very low O2 tension. Additionally, the high hemoglobin O2 content is not associated with a high partial pressure and is not able to drive diffusion of the O2 into the tissues, particularly ischemic tissue at the end of the capillary bed.

Other Beneficial Consequences Increasing the Effective O2 Deliver with Saturated Normal Saline Instead of Blood:

In diseases envisioned to be treated with the system of the present application that is caused by occlusions in the blood vessel system, blood flow distal to this occlusion is dependent on collaterals: with the usual drop in tissue perfusion pressure, and in spite of local compensatory mechanisms of vaso-dilation and increased oxygen extraction, the effective oxygen delivery is inadequate. Useful O2 is determined not only by O2 content of the blood, but by the rate of delivery of the blood to the tissue. The infused fluid may also dilute the whole blood, and lower the viscosity which will increase flow at a given pressure. This is particularly true in ischemic tissues where the perfusion pressure is low, and the flow is directly related to the effective viscosity of the fluid. Whole blood has a viscosity that is about eight times that of normal saline. The apparent lower viscosity of blood is in large part by having a lower hematocrit in the vessels that are smaller than 300 microns in diameter—this apparent breach of the law of continuity is done by having the plasma circulate almost 33% faster through the circulation (Fåhræus effect). Thus any O2 delivered in this supersaturated O2 normal saline may be delivered at a much higher rate than the whole blood it is diluting. In ischemic tissues, the local perfusion pressure is low, the vessels are maximally dilated, and the viscosity of the fluid is the major rate limiting factor. This device and method modifies the viscosity and thus circulation flow rate in a favorable direction.

Using this Method and Device in Conjunction with the Hybernia System:

The disclosed device is envisioned to be used as part of the Hybernia catheter cooling system in the preferred embodiment. In these instances, the temperature of the tissue may be decreased by about 5-7 C.°. With a reduced tissue metabolic rate, the need for O2 decreases at about 8-14%/degree C.° or at least about 40% from baseline. The Hybernia catheter system gives information related to the target tissue temperature, metabolism, and blood flow useful in determining optimal and safe gas content and flow rate.

Avoiding Symptomatic Bubbles:

If the fluid is saturated only to total of 750 mm Hg (i.e., the local barometric pressure the patient is under), and at the 37.8° C. (i.e., the patients core temperature), bubble development can be delayed and device and method may be safely used in this mode in a normal catheter. Splurging of N2 is likely to be minimal. The amount of O2 that can be delivered is limited, as seen in FIG. 4, but clinically important: returning the O2 saturated fluid in the catheter, as proposed in this application, to fluid in the blood stream which is at a higher temperature (0°->33° vs 37° C.°) may cause desaturation and excess O2 to bubble. Additionally, if the fluid is re-gassed under higher pressures than atmospheric pressure, there may be excess O2. Factors mitigating this can be addressed.

These factors may include: 1) O2 metabolism is extremely active, and the O2 depleted first from the blood stream is the dissolved O2 in the plasma, and not that carried on the hemoglobin. Nitrogen bubbles in the blood stream languish in the blood vessels nearly indefinitely causing decompression sickness. However, symptomatic O2 emboli after hyperbaric treatment with O2 partial pressure 5-10 times greater than what is discussed herewith is unheard of except in rare experimental conditions such as mixed gas transitions during decompression (reported cases under exceptional experimental conditions such as noble mixed gas transitions decompression from very high pressures). It is very likely that O2 bubbles do occur and are preferentially metabolized, and that their low viscosity does not delay or hinder circulation in any way. 2) The disclosed system may be configured to limit the delivered O2 to what can be metabolized. This limit can be set beforehand, and kept below the tissue O2 delivery requirements. Additionally, this can be calculated by a controller, as part of an infusion rate algorithm. 3) A O2 supersaturated saline infusion may be mixed with whole blood. The whole blood has additional O2 carrying capacity, in the form of a) little CO2, and H2O vapor pressure of the dissolved gases, b) unbound hemoglobin, and c) additionally the effect of lower temperature [30-33° C.] on the condition of: i. increasing the solubility of O2 in plasma and tissue, and ii. left shift of hemoglobin dissociation curve with lower temperature (Haldane effect). 4) The de-gassing is also important as dissolving additional O2 without de-gassing the N2 could in some instances lead to the formation of both O2 and N2 bubbles. N2 bubbles are toxic and dangerous. 5) Should O2 bubbles occur, the partial pressure of these bubbles may be atmospheric or about 750 mm of Hg, creating a huge gradient between them and the tissue, profoundly increasing passage of the gas into the tissue and quickly dissipating the bubbles. Venous return bubbles, common in decompression illness is not likely using the disclosed devices, as the O2 would be taken up by the O2 depleted hemoglobin of the venous blood.

Avoiding Detrimental Unintended Consequences Such as Oxygen Toxicity and Corrosion:

O2 toxicity is a complex phenomenon related to free radical or reactive oxygen species (ROS) created during O2 metabolism and by immune cells. The device is operable to allow the simultaneous infusion of ROS scavengers and enzymes, and key bio-signals such as NO that have been deleted by the ROS. Additionally, it should be noted that supersaturated O2 solutions, particularly at high pressures and high flow rates can be highly corrosive to metals and some plastics, and biocompatible corrosion resistant materials such as polyimide may need to be used.

CO2 is a product of oxygen and glucose metabolism. In humans, the blood CO2 content is approximately 2.7 mmol/100 ml at 40 mmHg (solubility in blood is 0.06 ml CO2/100 ml blood/mmHg). Only 5% (0.135 mmol/100 ml) of total blood CO2 is physically dissolved, whereas the majority is either joined with protein-carbamino compounds or is transported in the form of bicarbonate. Excess CO2 is usually removed in the lungs where CO2 diffuses from the capillary into the alveolar space and is exhaled. CO2 is involved in the regulation of blood acid-base homeostasis and is a potent vasodilator (increase in extracellular protons and decrease in local pH). When cerebral autoregulation is intact, an increase in blood CO2 level leads to dilation of cerebral vessels and, thus an increase in cerebral blood flow to maintain continuously sufficient oxygenation of brain tissue. This physiological coupling, also called cerebrovascular or vasomotor reactivity, may be exploited clinically to measure the natural capacity (or pathological lack thereof) of brain vessels to dilate under CO2 challenge, usually in conjunction with transcranial Doppler. Hereby, room air is enriched with 5-10% CO2 which leads to a higher alveolar CO2 partial pressure (PACO2) resulting in a counter-directed diffusion of CO2 into the capillaries, thus increasing the arterial CO2 partial pressure, e.g. >40 mmHg. This increase in PaCO2 is systemic, meaning this involves the entire body.

The present invention allows to selectively manipulate the arterial CO2 content of the target organ, such as the brain. Solubility of a gas, e.g. CO2, in water depends on temperature and pressure. The following table lists CO2 solubility in water at 1 atm (760 mmHg) at temperatures between 0 C and 37 C: (molar mass of CO2 is 44.01 g):

TABLE B

| Degree Celsius | CO2 solubility (g/100 ml H2O) | CO2 solubility (mmol/ 100 ml) |
| --- | --- | --- |
| 0 | 0.33 | 7.5 |
| 10 | 0.23 | 5.2 |
| 20 | 0.17 | 3.9 |
| 30 | 0.126 | 2.9 |
| 37 | 0.1 | 2.3 |

The presented values represent a theoretical maximum of CO2 dissolved in the infusate at 1 atm. When given selectively into the arterial organ bed, these amounts can be added to the baseline arterial CO2 content to increase PaCO2 in the target organ. Preparation with an additional gas, e.g. oxygen, at lower pressures for CO2 may result in controlled lower amounts of CO2 in the infusate (pO2>>pCO2). In practice, only a fraction of listed CO2 amounts is needed to achieve the desired effects, e.g., arterial vasodilation to increase organ blood flow or to test for vasomotor reactivity.

The presently disclosed systems may also mitigate the problem of iatrogenic air embolis by replacing N2 in the air with other gases that are less harmful. Inadvertent injection of air during intra-arterial injections for procedures is a serious problem that required highly trained professionals to use procedural vigilance to avoid. Additionally, in patients with right to left cardiac shunts—inadvertent venous air can pass into the arterial circulation and also lead to damaging air emboli. Particularly problematic is small bubbles initially retained on the wall of the infusion tubing when the lines are flushed with fluid, that later, during the procedure become dislodged and are injected into the artery. These adherent air bubbles consist of approximately 80% nitrogen, 20% oxygen, with small amounts of CO2 and water vapor. Most air emboli are small in size ranging from 0.05 to 5 mm in diameter but can be numerous. When injected into the blood stream, the O2 component is quickly metabolized and the CO2 and water vapor component quickly dissolve because of their very high solubility. The N2 component, the major bulk of the bubble is extremely slow to be desorbed-essentially acting as a case of iatrogenic-intra-arterial "bends."

Figure 5:
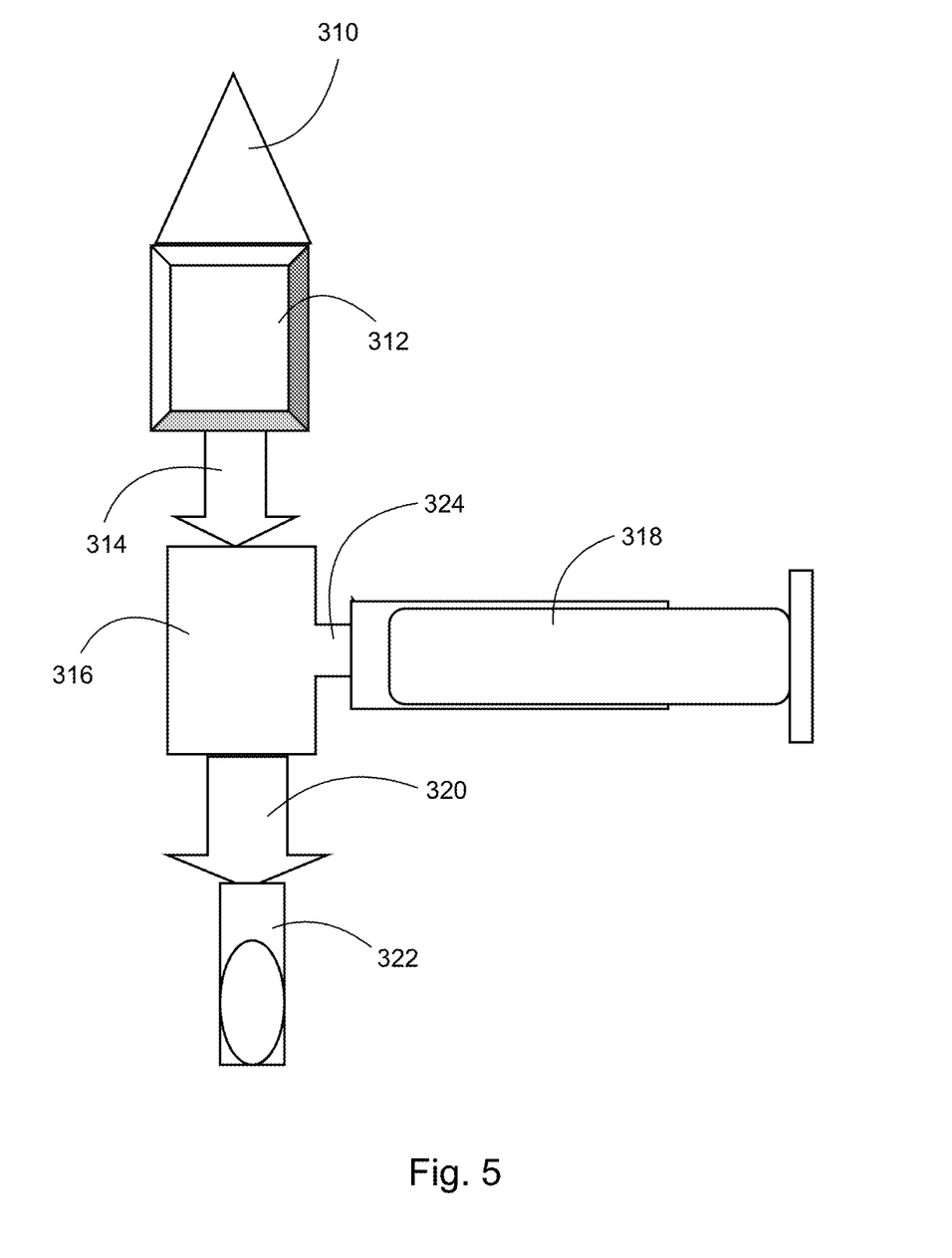
FIG. 5 depicts another system diagram according to at least one embodiment of the systems disclosed herein.

FIG. 5 presents a system according to another embodiment comprising a gas source tubing (not shown) connected to a connector 310 from which a source of gas, such as, O2 or Co2, may be provided. The connector 310 may run through a micropore filter 312 and a forward-only valve 314. The forward-only valve 314 may be connected to a T-valve 316. The T-valve includes a proximal arm 324 that is connected to a syringe 318. Syringe 318 may include a chamber comprising a volume corresponding to a line to be flushed. The T-valve 316 may be coupled to a second forward-only valve 320 that leads to a connector 322 for connection to a fluid line (not shown). Additionally, a one-way forward valve may be incorporated into the fluid line.

A gas source can be connected to the device at connector 310. The gas source may provide medical grade gas, and can come from either a tank or wall source, for O2, and tank for CO2. According to one embodiment, the gas may be provided, at a low pressure (e.g., 1.2 atm) and at a low flow rate, such as, 2-4 L/min. A fluid line to be flushed can safely and conveniently be attached to the system at connector 322. The disclosed system may flush room air in the fluid line to be replaced by the gas. Confirmation that the gas is flowing may be indicated by movement of the syringe 318. If the fluid line to be flushed is at some distance from the gas source (i.e., an extended fluid line), the syringe may be repeatedly cycled, thru aspiration and injection.

It can be seen from Table C below that 20 ccs of gas can flush commonly used flush lines, replacing the air with a chosen gas by a factor of 6.8 even when the longest and largest tube is used.

TABLE C

| tube diameter (mm) | length (mm) | Volume mm3 | syringe volume as multiples of tubing | | |
|---|---|---|---|---|---|
| | | | 5 | 10 | 20 |
| 3 | 75 | 530 | 9.4 | 18.9 | 37.7 |
| 3 | 100 | 707 | 7.1 | 14.2 | 28.3 |
| 3 | 150 | 1060 | 4.7 | 9.4 | 18.9 |
| 5 | 75 | 1472 | 3.4 | 6.8 | 13.6 |
| 5 | 100 | 1963 | 2.5 | 5.1 | 10.2 |
| 5 | 150 | 2944 | 1.7 | 3.4 | 6.8 |

According to another embodiment, a fluid line may be flushed with de-gassed fluid produced by the system described with respect to the description of FIG. 1. The de-gassed fluid can absorb and thus mitigate some unintentional retained gas.

FIGS. 1 through 5 are conceptual illustrations allowing for an explanation of the present invention. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

It should be understood that various aspects of the embodiments of the present invention could be implemented in hardware, firmware, software, or combinations thereof. In such embodiments, the various components and/or steps would be implemented in hardware, firmware, and/or software to perform the functions of the present invention. That is, the same piece of hardware, firmware, or module of software could perform one or more of the illustrated blocks (e.g., components or steps). In software implementations, computer software (e.g., programs or other instructions) and/or data is stored on a machine readable medium as part of a computer program product, and is loaded into a computer system or other device or machine via a removable storage drive, hard drive, or communications interface. Computer programs (also called computer control logic or computer readable program code) are stored in a main and/or secondary memory, and executed by one or more processors (controllers, or the like) to cause the one or more processors to perform the functions of the invention as described herein. In this document, the terms "machine readable medium," "computer readable medium," "computer program medium," and "computer usable medium" are used to generally refer to media such as a random access memory (RAM); a read only memory (ROM); a removable storage unit (e.g., a magnetic or optical disc, flash memory device, or the like); a hard disk; or the like.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

What is claimed is:

1. A system for infusing medical liquid with gasses, the system comprising:
a gas source;
a vacuum pump;
a temperature-controlled container including a fluid reservoir coupled to the gas source and the vacuum pump, a heating and cooling system, and a sonicator; and
a controller configured to:
de-gas a non-heme liquid in the fluid reservoir by heating the non-heme liquid until it reaches a given temperature and activating the vacuum pump therewith degassing the heated non-heme liquid;
re-gas the de-gassed non-heme liquid in the fluid reservoir by cooling the non-heme liquid until the liquid reaches a given cooling temperature, releasing gas from the gas source to the fluid reservoir via a first fluid line therewith increasing pressure of the cooled non-heme liquid, and exposing the non-heme liquid to the gas at the increased pressure for a period of time for the gas to saturate the non-heme liquid; and
deliver the re-gassed non-heme liquid from the fluid reservoir to a catheter via a second fluid line.

2. The system of claim 1 wherein the controller is further configured to de-gas the non-heme liquid in the fluid reservoir by enabling the heating and cooling system to heat the fluid reservoir, and activating the sonicator to sonificate the fluid reservoir.

3. The system of claim 1 wherein the controller is further configured to re-gas the de-gassed non-heme liquid in the fluid reservoir by enabling the heating and cooling system to cool the fluid reservoir, and activating the sonicator to sonificate the fluid reservoir.

4. The system of claim 1 wherein the gas comprises a gas selected from the group consisting of oxygen, carbon dioxide, and nitric oxide.

5. The system of claim 1 further comprising sensors to detect bubbles, gas concentration, and temperature of the non-heme liquid.

6. The system of claim 1 further comprising a device that flushes the first fluid line and the second fluid line with a gas that is capable of being metabolized, soluble, and non-toxic.

7. The system of claim 6 wherein the gas comprises a gas selected from the group consisting of carbon dioxide and oxygen.

8. The system of claim 1 wherein the controller is further configured to flush the first fluid line and the second fluid line with the non-heme liquid subsequent to de-gassing the non-heme liquid.

9. The system of claim 1 wherein the controller is further configured to re-gas the de-gassed non-heme liquid into a mono-saturated fluid.

10. The system of claim 1, wherein the non-heme liquid comprises saline.

11. The system of claim 1, wherein the non-heme liquid is de-gassed and re-gassed to result in the non-heme liquid being mono-saturated with the gas from the gas source.

12. The system of claim 1, wherein the non-heme liquid is heated up to 40 deg. C., and cooled no less than about 0 deg. C., and wherein the non-heme liquid delivered contains up to 45% of the gas normally carried by arterial blood.

13. Non-transitory computer readable media comprising program code that when executed by a programmable processor causes execution of a method for infusing medical liquid with gasses, the computer readable media comprising:
computer program code for de-gassing a non-heme liquid in a fluid reservoir by heating the non-heme liquid until it reaches a given temperature and activating the vacuum pump therewith degassing the heated non-heme liquid, and is comprised in a temperature-controlled container that includes a heating and cooling system and a sonicator;
computer program code for re-gassing the de-gassed non-heme liquid in the fluid reservoir by cooling the non-heme liquid until the liquid reaches a given cooling temperature, releasing gas from the gas source to the fluid reservoir via a first fluid line therewith increasing pressure of the cooled non-heme liquid, and exposing the non-heme liquid to the gas at the increased pressure for a period of time for the gas to saturate the non-heme liquid; and
computer program code for delivering the re-gassed non-heme liquid from the fluid reservoir to a catheter via a second fluid line.

14. The non-transitory computer readable media of claim 10 further comprising computer program code for de-gassing the non-heme liquid in the fluid reservoir by enabling the heating and cooling system to heat the fluid reservoir and activating the sonicator to sonificate the fluid reservoir.

15. The non-transitory computer readable media of claim 13 further comprising computer program code for re-gassing the de-gassed non-heme liquid in the fluid reservoir by enabling the heating and cooling system to cool the fluid reservoir, and activating the sonicator to sonificate the fluid reservoir.

16. The non-transitory computer readable media of claim 13 wherein the gas comprises a gas selected from the group consisting of oxygen, carbon dioxide, and nitric oxide.

17. The non-transitory computer readable media of claim 13 further comprising computer program code for detecting bubbles, gas concentration, and temperature of the non-heme liquid.

18. The non-transitory computer readable media of claim 13 further comprising computer program code for flushing the first fluid line and the second fluid line with the non-heme liquid subsequent to de-gassing the non-heme liquid.

19. The non-transitory computer readable media of claim 13 further comprising computer program code for re-gassing the de-gassed non-heme liquid into a mono-saturated fluid.

* * * * *